United States Patent
Tranzeat

(10) Patent No.: US 8,043,569 B2
(45) Date of Patent: Oct. 25, 2011

(54) DEVICE FOR DISPENSING A VOLATILE SUBSTANCE

(75) Inventor: Lyse Tranzeat, West Drayton (GB)

(73) Assignee: Firmenich SA, Geneva (CH)

( * ) Notice: Subject to any disclaimer, the term of this patent is extended or adjusted under 35 U.S.C. 154(b) by 574 days.

(21) Appl. No.: 12/139,170

(22) Filed: Jun. 13, 2008

(65) Prior Publication Data

US 2008/0311008 A1    Dec. 18, 2008

(30) Foreign Application Priority Data

Jun. 14, 2007   (EP) .................................. 07110232

(51) Int. Cl.
*A62B 7/08* (2006.01)
(52) U.S. Cl. ..................................................... 422/124
(58) Field of Classification Search .................. 422/124
See application file for complete search history.

(56) References Cited

U.S. PATENT DOCUMENTS

| | | | | |
|---|---|---|---|---|
| 5,480,591 | A | * | 1/1996 | Lagneaux et al. ............... 261/30 |
| 6,103,201 | A | | 8/2000 | Green .............................. 422/124 |
| 2002/0197189 | A1 | * | 12/2002 | Lua ................................ 422/124 |
| 2003/0108461 | A1 | * | 6/2003 | Lo ................................. 422/305 |
| 2004/0184969 | A1 | | 9/2004 | Kotary et al. ................... 422/124 |
| 2006/0043619 | A1 | | 3/2006 | Brown et al. ..................... 261/19 |

FOREIGN PATENT DOCUMENTS

| | | |
|---|---|---|
| EP | 0 672 425 B1 | 6/1999 |
| EP | 1 522 320 A1 | 4/2005 |
| GB | 2277266 * | 10/1994 |
| WO | WO 2004/006968 A1 | 1/2004 |
| WO | WO 2005/030277 A1 | 4/2005 |
| WO | WO 2006/061803 A1 | 6/2006 |

OTHER PUBLICATIONS

European Search Report 07110232.1 Dated Sep. 18, 2007.

* cited by examiner

*Primary Examiner* — Walter Griffin
*Assistant Examiner* — Christopher VanDeusen
(74) *Attorney, Agent, or Firm* — Winston & Strawn LLP

(57) ABSTRACT

The present invention relates to the field of perfumery and more precisely it concerns a device, and the consumer articles associated therewith, for dispensing an active composition into the surrounding space. The device includes an active liquid, a reservoir holding the active liquid, a wick-/emanator structure composed of a wicking part and an emitting part, the latter having an evaporative surface to be directly exposed to the surrounding space when the device is activated and being housed in a moveable housing assembly, activation of the device occurring without need to removing the housing assembly and or the wick-/emanator structure, the device further comprising a rotor arranged in a manner providing for rotation of wicking or emitting parts to allow forced evaporation of the active volatile upon activation of the device.

19 Claims, 7 Drawing Sheets

DEVICE FOR DISPENSING A VOLATILE SUBSTANCE

TECHNICAL FIELD

The present invention relates to the field of perfumery and more precisely it concerns a device, and the consumer articles associated therewith, for dispensing an active volatile substance into its surroundings, particularly in an enclosed atmosphere. The device of the invention is an air-freshener device comprising a reservoir for containing an active liquid having a specific volatility and containing a substance that one desires to disseminate into the atmosphere, and a wick/emanator structure composed of a part able to soak in the liquid volatile and be impregnated therewith and an emitting part, the latter having an evaporative surface exposed to the surrounding space, and optionally a specific absorbency and weight per unit of the evaporative surface. At least a part of the wick/emanator structure is intended for connection to a rotor member or another means for engaging the part into movement, particularly rotation, and thus force enhanced evaporation of the volatile substance from the evaporation surface of the emanator, relative to the evaporation that would have been observed in the absence of such means.

PRIOR ART

Devices for dispensing an active volatile liquid in the surrounding space have been known for a long time. One type of such devices are the so-called wick-based devices, which all comprise a reservoir, a wick plunging into a volatile liquid contained in the reservoir and an emanating body or surface from which the active liquid evaporates.

Many air-freshener devices of the wick type have been described in the prior art. Although many such devices work by unforced or natural evaporation only, due to the volatility of the liquid being diffused into the surrounding atmosphere, it is desirable to increase the evaporation by providing evaporation forcing means, for example an external fan or other mechanical means increasing ventilation and thus forcing evaporation of the volatile substance from the emitting surface, or yet means providing for electrical heating of the evaporating surface of the porous wick/emanator element(s), thus accelerating diffusion of the substance.

Forced ventilation of the emanating surface has required in the past the use of parts separate from the basic components of the diffusing device, i.e. the container comprising the substance to be diffused, the wick member able to absorb the liquid, and the emanator surface from which the liquid substance diffuses and evaporates into the device's surroundings. The above-mentioned separate parts have typically been formed of fans which are battery or electrically powered. Typical recent examples of such devices are described, amongst others, in patent documents WO 2005/030277 A1 and US 2006/0043619 A1. In the first of these, there is described a device provided with an electrically-powered fan acting on an evaporation surface that is essentially planar and has an orientation generally parallel to the direction of the forced ventilation provided by the fan, whilst the teaching of US 2006/0043619 is representative of more conventional fan operated air-fresheners.

Many other examples of fan operated devices can be found in the prior art but they all require rotating or moving parts that are independent and separate from the wick/emanator assembly and structure and which increase the cost of the device relative to those which rely on unforced evaporation.

Alternative devices have been known to resort to the use, as taught for example in European patent application EP 672 425, of a rotating cartridge carrying a recipient for the liquid whose vapors are to be diffused, which recipient is closed by a membrane capable of letting the volatile substance vapors diffuse through it, whilst keeping the liquid inside the recipient. According to this document, the cartridge is drawn into rotation and this allows the membrane to be in constant contact with the liquid and to constantly diffuse into the atmosphere its vapors. A separate rotating helix increases the air flux in front of the membrane and ensures a smooth diffusion of the vapors outside the cartridge. Once again, separate parts are provided to ensure increased air flux which in turn enhances evaporation of the liquid from the recipient. It is to be noted moreover that the evaporation surface has to be adapted to the form of the opening of the liquid container and must be lodged in such a way as to prevent spillage of the liquid. This effectively restricts the shape and area of the emanating surface.

In another known solution to the problem of increasing ventilation in this context, U.S. Pat. No. 6,103,201 to Green, has taught the use of a rotor made of scent-bearing material and adapted to be connected to room ventilation systems, but such a rotor cannot be connected to a reservoir containing the volatile substance so as to allow constant replenishing of the evaporation surface in volatile material, necessary for a linear and sustained release thereof over time, during the normal and/or forced evaporation periods.

SUMMARY OF THE INVENTION

The present invention aims at improving over all the known devices by providing a diffusing device and more particularly an air freshener that is efficient in delivering a constant and linear amount of active composition over the lifetime of the device, is particularly adapted to be used with substantially non-aqueous volatile compositions, thus dispensing the use of large amounts of surfactants, although being also adapted to the diffusion of other types of partially aqueous volatile liquids, and which requires a smaller number of parts to be manufactured and assembled, as compared to other powered air fresheners having an enhanced capability of volatile substance evaporation. To the best of our knowledge, the prior art has never taught or suggested a solution such as described hereafter to the problem of increasing ventilation of the evaporation surface in a wick type air-freshener and thus increase the diffusion of the active substance into the device's surroundings.

The present invention aims at dispensing with such separate independent moving parts, while still providing for enhanced evaporation of the volatile substance to be dispensed into the atmosphere. In particular, the device of the present invention comprises a reservoir containing the active volatile substance, an emanating member carrying the evaporation surface; a wick member adapted to be lodged in the device through the opening of the reservoir's upper part in a position allowing it to be impregnated with the volatile substance and to be in contact with the emanating member such that, upon activation of the device, the emanating member and the wick member are lodged in the device in a position allowing the wick member to be in contact with the active volatile substance and to cause the emanating member to be impregnated therewith; and means allowing direct movement, and more particularly rotation, of the evaporating surface for the volatile substance, thus dispensing without the use of a separate fan, helix or other device to increase air flux and ventilation of the emanating or diffusing surface. In addition, it is possible to use a diffusing surface with a variable area of diffusion, not limited to the shape and diameter of the liquid container opening, as is the case in the prior art described in EP 672 425.

BRIEF DESCRIPTION OF THE DRAWINGS

Preferred, non-limiting features of the invention are disclosed in the appended drawing figures, of which.

DETAILED DESCRIPTION OF THE PREFERRED EMBODIMENT

Figure 1:
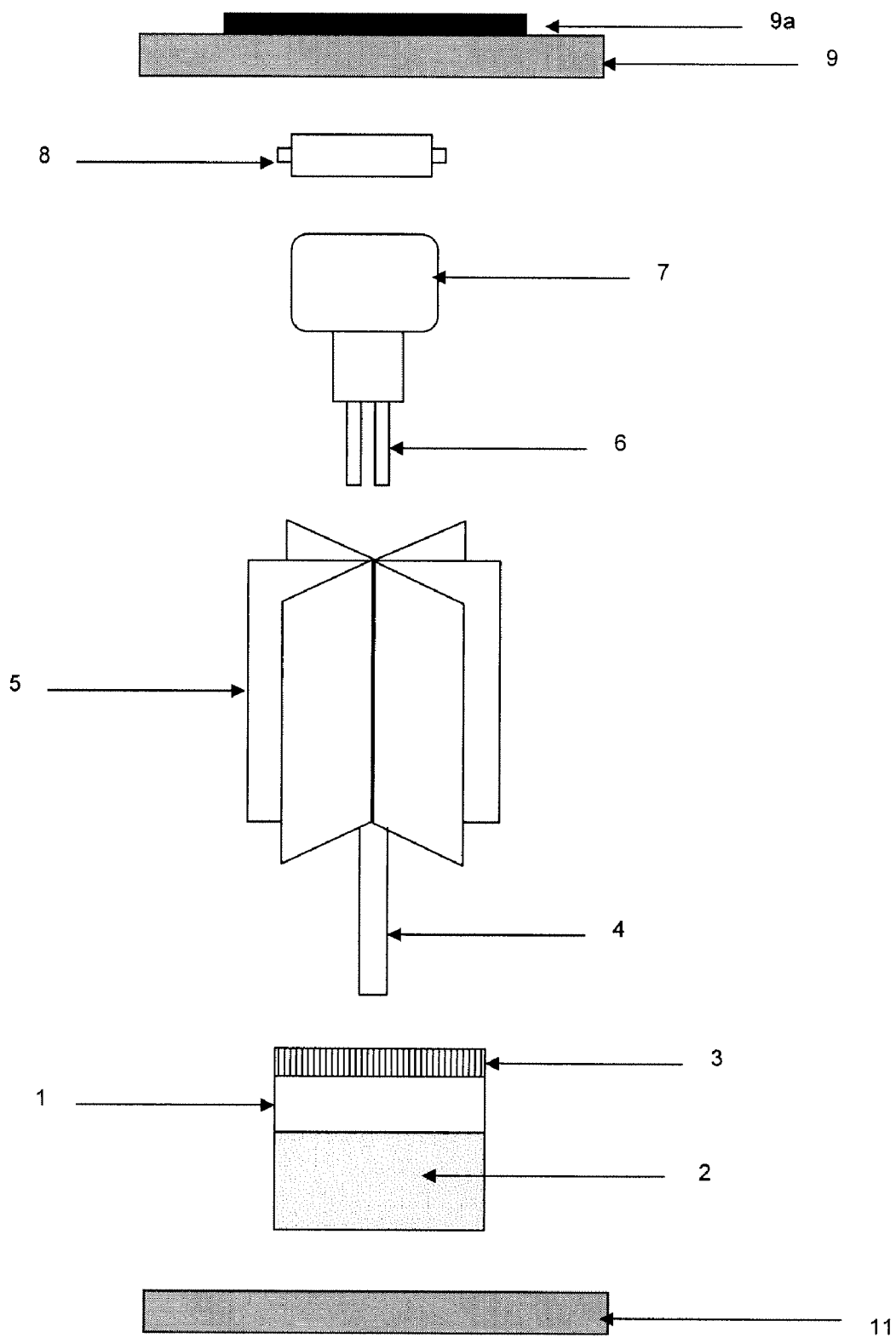
FIG. 1 is an exploded view, partially in cross section, of one embodiment of the device according to the invention, showing the various parts to be assembled.

The aim of the present invention is to provide a device for the diffusion of a volatile substance into the device's surroundings. The device of the invention is more particularly an air freshener device of the wick type able to diffuse an active volatile liquid in the surrounding space, rooms, cupboards or other enclosed spaces possibly provided with a light source, the device having an essentially linear performance, i.e. diffusing a volatile substance at approximately constant rate during each period of unforced or forced evaporation of the active volatile.

This is achieved by providing a device for dispensing an active volatile substance into a surrounding atmosphere, provided with means for forced ventilation of an evaporation surface impregnated with the volatile substance, the device comprising:

a reservoir containing the active volatile substance and having an upper part equipped with an opening optionally covered with a cap;

an emanating member having an evaporation surface formed of a material capable of being impregnated with the active volatile substance upon activation of the device and of allowing evaporation thereof into the device's surroundings (i.e., the air);

a wick member formed of, or carrying, a porous material part capable of being impregnated with the active volatile substance, the wick member being adapted to be lodged in the device through the opening of the reservoir's upper part, in a position allowing it to be impregnated with the volatile substance and to be in contact with the emanating member; wherein, upon activation of the device, the emanating member and the wick member are lodged in the device in a position allowing the wick member to be in contact with the active volatile substance and to cause the emanating member to be impregnated with the active volatile substance, and means capable of causing movement of at least the emanating members for a determined period of time, relative to the recipient comprising the active volatile substance, so as to cause forced ventilation of the evaporation surface of the emanating member.

According to a specific embodiment of the device of the invention, there is further provided a housing part or assembly covering at least the emanating member, the housing part or assembly comprising means to allow diffusion of the active volatile substance into the device's surroundings upon its activation. The housing assembly may comprise two vertical cylindrical parts, an internal element and an external element thereof, the two elements being provided with openings or vents, the elements being moveably arranged and able to slide relative to each other, preferably coaxially, upon activation of the device, to allow partial or total overlap of the inner and outer vents and thus increased exposure of the diffusing surface to the surroundings of the device.

According to advantageous embodiments of the invention, the active volatile is selected amongst the group of fragrance, deodorizing, sanitizing, insect repellent compositions, and their mixtures. It is clear however that other volatile or partially volatile substances may be diffused into the atmosphere from the device of the invention, provided they are adapted to impregnate the wick and diffuse from the porous emanating member. Essentially, the device of the invention shall carry any substance able to provide a useful and/or beneficial quality to the surrounding air, by for example improving its odor quality, purity or sanitized quality.

Advantageously, the movement causing means includes a rotating motor connected to at least the emanating member and able to cause rotation thereof. Typically, the device is a battery or electrically powered air freshener, but it may also conveniently be a solar powered one. The latter embodiment of the invention has obvious energy supply advantages, as well as allowing its use even in places where electrical energy is not readily available.

By "active volatile substance, composition or liquid" it is meant herein a liquid composition which is at least partially volatile, i.e. can evaporate, and which is able to impart a benefit to the atmosphere or space surrounding the device. It may be a substantially non-aqueous liquid comprising odorant materials, or it may also contain a certain amount of water.

The reservoir chamber has the function of storing the active volatile liquid composition or, as also referred to from now on, the "active composition" prior to activation of the device and, after activation, the remainder thereof which has not been absorbed on the wick-emanator assembly and diffused as time goes by.

The invention also relates to specific embodiments wherein the wick member is lodged within a guiding or supporting structure disposed within the housing assembly, possibly a shaft type structure that also supports the emitting/evaporation member. This wick member guiding or supporting structure may be axially disposed within the housing assembly.

The reservoir will typically be provided with means to prevent evaporation of the active composition from the reservoir before activation thereof. According to preferred embodiments, the reservoir's opening carries a lid or barrier formed of foil and hermetically fastened thereto before activation of the device. The foil is intended for removal upon activation, or optionally for being perforated by the wick member or a wick-guiding member. This barrier then has the function of preventing evaporation of the volatile composition before activation of the device and is removed or perforated when the device is activated to diffuse the active volatile.

The reservoir may also carry a cap or lid assembly. The latter may be provided with means such as slots or other structures, possibly molded thereon, for accommodating and securing the lower end of the emanating surface or emanator member on top of the reservoir and extending from it. According to advantageous embodiments, the emanator will be arranged on a support structure, namely a shaft, provided with a hollow cavity adapted for lodging the wick member. Details of the manner in which the latter may be realized are presented in the examples described further on, but also as taught in International patent application WO 2006/061803, owned by the present applicant.

As previously indicated, the emanator and wick members, or their assembly, may be lodged within the device's housing assembly. They are preferably coaxially arranged (although such an axis does not have to be vertically arranged above the liquid container) and lodged within the housing structure, possibly cylindrical, which can typically be fastened to the reservoir's cap.

Whenever a housing is provided, its shape can however be any, provided that it is adapted to allow free movement, and more typically rotation, of the wick/emanator structure, or at least of the emanating member lodged inside the housing.

Of course, it is also possible to have a device according to the invention that is not provided with a housing. Since the emanator and wick members are generally only put into contact with the active volatile substance contained in the reservoir upon activation of the device, a housing is not needed for the purposes of the invention.

In some embodiments of the device, the container holding the active volatile substance is provided in a separate packaging from that of the wick/emanator assembled structure, or even from the separate wick and emanator member packagings. The reservoir will be typically hermetically closed and caped before activation of the device. The wick/emanator member will be shaped so as to allow the user to assemble them together, and then lodge the assembly thus obtained on the reservoir opening in such a manner as to allow the absorbing surface of the wick to be plunged into the active substance when the device is activated.

For example, the reservoir may be provided with a foil hermetically closing its opening, and the wick member provided with a pointed extremity able to perforate the foil to allow immersion of the wick into the active composition. Perforation of the hermetic barrier of foil may be carried out by the user, or may be caused by movement of the housing structure to which the wick/emanator assembly is connected in a known manner, as described for example in WO 2006/061803.

It must be noted as well that the activation of the device is typically a one-off action not able to "enhance or force ventilation" of the diffusing or emanating surface in the sense of the invention as defined in the claims, i.e., the movement of the housing structure, or of the two parts thereof able to slide relative to each other as mentioned earlier on, does expose this emanating surface to the surrounding atmosphere but does not increase the ventilation of the surface as compared to prior known devices and does not provide for "forced ventilation" as is presently understood. The latter is in fact understood as being ventilation caused by repeated movement of the emanating member, or of the wick/emanating structure or assembly, over a certain period of time, which movement is controlled by the user as explained hereafter, or possibly caused by pulsed auctioning of the means capable of directly acting on the emanating member or assembly.

The wick/emanator assembly may be formed of a single piece, part of which is plunged into the active composition once the device is activated. Preferably, it will formed of two pieces arranged in such a manner that at least the emanating part can rotate freely upon activation of the powering means, namely a motor, to which it is connected, so as to provide forced and enhanced evaporation of the composition to be diffused into the atmosphere surrounding the air-freshener device, without necessarily engaging the wick part into the same rotating movement. In some embodiments however, both parts may be rotated.

There are therefore many ways in which these two elements forming the wick/emanator assembly can be designed and optionally lodged in a housing assembly, provided that at least the emanating member can rotate upon action from the rotor, or other movement causing means, to which it is connected.

An essential element of the device is therefore a motor that can be activated preferably by means of an on/off button or timer accessible from the external surface of the device. According to preferred embodiments, this is a rotor powered via a battery supplied with electrical or solar energy. It is also possible to power the battery by means of a manually activated wind-up system.

When solar powered means are provided, the air freshener device of the invention may be equipped with a solar cell or panel capable of accumulating energy from day or sunlight, or from a source of artificial light, and connected to the battery as shown specifically in some of the examples presented further on.

Of course, the movement of the emanating member and diffusing surface thereof need not be a rotation. For example, alternative movement may be of an oscillation or pendulum-like nature, which advantageously reduces the friction on the active composition and thus requires less energy to be operated.

As previously indicated, the volatile composition contained in the reservoir is generally prevented from evaporation before activation of the air freshener, to ensure that no substantial loss thereof occurs during storage. The device is therefore generally provided with means for hermetically closing the aperture of the reservoir and/or for preventing the vents of the inner and outer hollow vertical parts of the housing assembly from coinciding and thus allowing evaporation of the active composition, whenever such a housing is provided.

Moreover, the invention also includes packaged devices wherein the reservoir, generally containing the active volatile substance, is hermetically closed as described above and packaged separately from the other parts of the device. Such an embodiment of the invention presents the advantage of being re-chargeable, the supply of active volatile being able to be replaced by a new filled reservoir when the prior used one has been emptied through evaporation of the active composition or when the user desires to replace the latter even if not empty, to change for example the quality and/or nature of the active substance, and namely the scent, being diffused.

Activation of the device upon use can occur in many ways, and a large variety of these are exemplified in International patent publication WO 2006/061803. All such examples of devices and activation mechanisms, which are compatible with the incorporation of a moveable and more particularly rotatable evaporation surface for the active composition, powered by a rotor as described above or by any other auctioning means, can be used according to the present invention. The person skilled in the art is able to envisage such movement mechanisms as a function of the shape of the emanating member or assembly and the type of movement selected therefore, namely rotating, oscillating or pendulum-like for example.

For operating the device, in case of rotation, once the device is in the active position, turning on the rotor will provide for rotation of at least the emanating surface member of the wick/emanating structure and the user will be able to use unforced or forced evaporation, as desired, by activating or not this movement. Such activation may also be done periodically, for a selected amount of time, either through direct user action or for example via a pulsing device automatically set to become active at certain time intervals, piloted by a timer for example.

In specific embodiments of possible device activation means, there will be provided, possibly on the housing assembly, moveable means capable of causing one-off movement of the upper part of the device, carrying the wick/emanator assembly, relative to the reservoir or its cap or capping assembly, so as to provide for perforation of the protecting hermetic barrier or seal of the reservoir's opening. Such moveable device activation means may for example consist of a slide member connected to at least one of the two parts of the housing assembly and able to move one of the two parts relative to the other. The slide may be installed vertically so as to provide for longitudinal movement of the two parts relative to each other. The wick member, or alternatively a guiding structure therefore, will then perforate the hermetic seal of the reservoir's opening upon activation of the device.

More commonly, the emanator and wick members shall not be part of a same piece or assembly, and it is then possible to have the wick already plunged inside the reservoir's liquid and to provide means allowing for the emanator member to come into contact with the wick upon activation of the device and thus be impregnated with active composition and be able to diffuse it over time from its evaporative surface. In these embodiments of the device, there are provided means to force this contact, which are typically lodged within the housing assembly, for example in the form of a spring lodged between the emanator member carrying the diffusing surface and the inside surface of a part capping the housing assembly of the device which houses the emanator.

According to other embodiments of the invention, the emanating member or emanator, and the wick member or wick, form a single piece or superstructure. The device will then be typically equipped with moveable device activation means causing the wick part of the superstructure to plunge in the volatile liquid when the device is activated, in a one-off movement.

Amongst such embodiments, there are provided those wherein one zone of the emanating piece can be deformed and made to plunge into the reservoir's liquid upon activation of the device to allow impregnation of the zone with the active composition and subsequent absorption thereof by the emanating surface for diffusion.

Alternatively, the device may be provided with a deformable housing assembly, such that, for activating the device, the user applies pressure on the housing assembly to force the wick zone of the emanator/wick assembly to pierce the barrier and plunge into the liquid to be diffused. The wick is then retained inside the liquid for the lifetime of the device by a variety of means, illustrated in the examples of WO 2006/061803, the contents of which are expressly incorporated herein by reference thereto. It goes without saying that such deformable housings can also be used with a two-piece wick/emanator assembly of the type previously mentioned.

In general, the essential parts of the device are formed by the reservoir containing the volatile active composition, a barrier to prevent evaporation of the latter prior to activation of the device, an absorption/diffusion member or members capable of being impregnated with the composition and of diffusing it into the surroundings once the device is activated, at least the diffusing part of the absorption/diffusion member being moveably, and more particularly rotatably, mounted in the device and connectable to a rotating motor or other motion causing means. This whole ensemble can be lodged in a housing assembly and is provided with device activating means that make it possible to activate the device can be activated without removal of the ensemble, i.e. all its parts above, from the housing, to allow diffusion of the composition.

Preferably, when a housing is provided, it is formed of two vertical parts able to horizontally slide relative to each other, thus allowing regulation of the surface of exposure of the evaporative surface of the emanating member to the surroundings by varying the partial or total coincidence of the diffusion vents on the two housing parts. The latter vents may be carved vertically or horizontally. The housing parts are typically made of plastic, possibly deformable, and may assume any shape that is adapted to the objective use of the device.

Convenient wick/emanator assemblies are emanating superstructures, adapted to be activated according to the invention, and acted upon via appropriate movement means capable of drawing at least the emanating part or member thereof into rotation, oscillation or pendulum-like movement, such as those formed as described for example in Applicant's International application WO 2004/006968, the contents of which are expressly incorporated herein by reference thereto. The materials for their realization are disclosed in the mentioned International application. Superstructure emanating members of this type, having a weight comprised between 80 and 1000 grams per square meter of evaporative surface, and an absorbency comprised between 0.01 and 0.1 grams of active volatile liquid composition per square centimeter of evaporative surface, are suitable for the purposes of the invention.

Amongst these, emanating members having an evaporative surface comprised between 50 and 400 $cm^2$, more preferably between 100 and 200 $cm^2$, are particularly useful embodiments thereof.

The examples presented further on show such devices comprising superstructure-type wick/emanator assemblies, as well as assemblies wherein the wick and the emanator are separate pieces, and the manner in which they may be incorporated in the devices of the invention.

The reservoir, and possibly a cap or lid therefore, are formed of materials compatible with the nature of the active composition and totally impermeable to the vapors of the latter. Preferably the reservoir chamber is made of a transparent or translucent material, so that a consumer can visually monitor the level of the active composition present in the reservoir chamber, and therefore know when the reservoir or the device according to the invention has to be replaced because exhausted, or because it is desired to use a different scent for example.

Suitable materials for the reservoir chamber and the reservoir chamber lid or cap, include glass, injection or thermoformed molded materials such as those obtainable from polymers like polyethylene, polypropylene, polystyrene, polyvinyl chloride, polyvinyl acetate, polyamide, polyacrylamide, polymethylacrylate, and the like.

It is also understood that the reservoir and the cap can be part of a single body.

According to a preferred embodiment of the invention, the composition to be contained in the reservoir is non-aqueous.

By a "non-aqueous" active volatile liquid composition or active composition it is meant here an active volatile liquid composition which is essentially devoid of, or contains only marginal amounts of, water, e.g. one may cite as example a composition which contains at most 10%, of its total weight, of water.

A preferred active composition is also surfactant free.

The active composition contains at least one active ingredient. The ingredient is capable of imparting a benefit to the device's surrounding space, namely an enclosed space, and may be accompanied by optional ingredients which can be beneficial to the active volatile material. In other words the active composition contains an active volatile material, comprising at least one ingredient, and optionally one or more ingredients selected from the group consisting of solvents, thickeners, anti-oxidants, dyes, bittering agents and UV inhibitors.

As the active volatile material, there can be used, for example, a perfume. Other suitable active volatile materials can be deodorizing or sanitizing agents or insect repellents or any other active materials capable of imparting perceptible and desirable benefits to the quality of the air into which they are diffused.

A preferred active volatile material is a perfume. As perfume there can be used any ingredient or mixture of ingredients currently used in perfumery, i.e. capable of exercising a perfuming action, meaning modifying or imparting the odor of the surrounding air. This means that a malodor counteracting composition, capable of reducing or suppressing a large variety of malodors, such as body malodor, tobacco malodor, kitchen or bathroom malodor for example, are also understood herein as being comprised in the "perfume", "fragrance" or "perfuming composition" definition. Often, such a perfuming composition will be a more or less complex mixture of ingredients of natural or synthetic origin. The nature and type of the ingredients do not warrant a more detailed description here, which in any case would not be exhaustive, the skilled person being able to select them on the basis of its general knowledge and according to intended use or application and the desired organoleptic effect, deodorizing, perfuming, sanitizing or other. In general terms, these perfuming ingredients belong to chemical classes as varied as alcohols, baldheads, ketenes, esters, ethers, acetates, nitrides, terrene hydrocarbons, nitrogenous or sulfurous heterocyclic compounds and essential oils of natural or synthetic origin. Many of these ingredients are in any case listed in reference texts such as the book by S. Arcade, Perfume and Flavor Chemicals, 1969, Montclair, N.J., USA, or its more recent versions, or in other works of a similar nature, as well as in the abundant patent literature in the field of perfumery and malodor counteraction. Many are known to possess malodor counteracting and/or antibacterial activity so that, in addition to being capable of perfuming, and thus imparting a pleasant smell to, the surrounding air, they also help purify and sanitize the latter, and/or remove any malodor (i.e. unpleasant smell) thereof.

Natural oils such as lavender, cedar, lemon and other essential oils and extracts are particularly preferred for advantageous embodiments of the invention.

Although special mention has been made hereinabove of the perfuming effect that can be exerted by the devices of the invention, the same principles apply to analogous devices for the diffusion of deodorizing or sanitizing vapors, the perfume being replaced by a deodorizing composition, an antibacterial, an insecticide, an insect repellent or an insect attractant, or a so-called mothproofed device. By the term "sanitizing vapors", we refer here not only to the vapors of those substances which can enhance the degree of acceptance of the air surrounding the observer, but also to those substances which can exert an attractant or repellent effect towards certain species of insects, for instance towards houseflies or mosquitoes, or else, which can have bactericide or bacteriostatic activity. It goes without saying that mixtures of such agents can also be used.

The total amount of active volatile material in the active composition may be comprised between 20% and 100%, preferably between 30% and 70%, of the weight of the active composition.

As anticipated above, the active composition may also contain some optional ingredients acting as, for example, solvents, thickeners, anti-oxidants, dyes, bittering agents and UV inhibitors.

As non-limiting examples of useful UV-inhibitor ingredients, one can cite benzophenones, diphenylacrylates or cinnamates such as those available under the trade name UVINUL® (origin: BASF AG).

The total amount of UV-inhibitors present in the active composition may vary between 0.0% and 0.5%, preferably between 0.01% and 0.4%, the percentages being relative to the total weight of the active composition.

The presence of one or more solvents may be useful to have a single-phase liquid and/or to modulate the speed of evaporation of the active material into the surrounding air. The solvents may belong to the families of isoparaffins, paraffins, hydrocarbons, namely glycols, glycol ethers, glycol ether esters, esters or ketones.

Examples of suitable commercially available solvents are known under the tradename ISOPAR® H, J, K, L, M, P or V (isoparaffins; origin: Exxon Chemical), NORPAR® 12 or 15 (paraffins; origin: Exxon Chemical), EXXSOL® D 155/170, D 40, D 180/200, D 60, D 70, D 80, D 100, D 110 or D 120 (de-aromatized hydrocarbons; origin: Exxon Chemical), DOWANOL® PM, DPM, TPM, PnB, DPnB, TPnB, PnP or DPnP (glycol ethers; origin: Dow Chemical Company), EASTMAN® EP, EB, EEH, DM, DE, DP or DB (glycol ethers; origin: Eastman Chemical Company), DOWANOL® PMA or PGDA (glycol ether esters; origin: Dow Chemical Company) or EASTMAN® EB acetate, EASTMAN® DE acetate, EASTMAN® DB acetate, EASTMAN® EEP (all glycol ether esters; all origin: Eastman Chemical Company) or yet 3-methoxy-3-methyl-1-butanol, also known as solvent MMB and available from a variety of suppliers.

Other examples of solvents useful to the invention are dipropylene glycol, propylene glycol, ethylene glycol ethyl ether acetate, ethylene glycol diacetate, isopropyl myristate, diethyl phthalate, 2-ethylhexyl acetate, methyl n-amyl ketone or di-isobutyl ketone.

Preferred solvents include DOWANOL® DPM, DPnB or DPnP, as well as 3-methoxy-3-methyl-1-butanol.

The total amount of such solvents present in the active composition may vary between 0.0% and 80%, preferably between 30% and 70%, the percentages being relative to the weight of the active composition. Preferred perfuming compositions will comprise at least 30% by weight of perfume and not more than 70% by weight of any such solvents.

Preferably, at least 60% of total weight of the active composition is made of ingredients having a vapor pressure comprised between 4 Pa and 270 Pa, the vapor pressure being measured at 20° C. and a pressure of 760 mmHg. The described requirement in the formulation of the active composition ensures that a relatively constant composition is maintained over the lifetime of the device and that the active composition evaporates at a relatively steady rate during the life of the product.

Most preferably, at least 80% of total weight of the active composition is made of ingredients having a vapor pressure comprised between 4 Pa and 270 Pa.

As non-limiting examples of useful antioxidant ingredients, one can cite the sterically hindered amines, i.e. the derivatives of the 2,2,6,6-tetramethyl-piperidine, such as those known under the tradename UVINUL® (origin: BASF AG) or TINUVIN® (origin: Ciba Specialty Chemicals), as well as the alkylated hydroxyarene derivatives, such as butylated hydroxytoluene (BHT).

The total amount of antioxidants present in the active composition may vary between 0.0% and 10%, preferably between 1% and 4%, the percentages being relative to the weight of the active composition.

Dyes are other optional ingredients of the active composition. Suitable dyes are oil-soluble and can be found in the Colour Index International, published by The Society of Dyers and Colourist. Non-limiting examples of suitable dyes are derivatives of the anthraquinone, methine, azo, triarylmethane, triphenylmethane, azine, aminoketone, spirooxazine, thioxanthene, phthalocyanine, perylene, benzopyran or perinone families.

Examples of such dyes which are commercially available are known under the tradename SANDOPLAST® Violet RSB, Violet FBL, Green GSB, Blue 2B or SAVINYL® Blue RS (all anthraquinone derivatives; origin: Clariant Huningue S.A.), OILSOL® Blue DB (anthraquinone; origin: Morton International Ltd.), SANDOPLAST® Yellow 3G (methine; origin: Clariant Huningue S.A.), SAVINYL® Scarlet RLS (azo metal complex; origin: Clariant Huningue S.A.), OILSOL® Yellow SEG (monoazo; origin: Morton International Ltd.), FAT ORANGE® R (monoazo; origin: Hoechst AG), FAT RED® 5B (diazo; origin: Hoechst AG), NEOZAPON® Blue 807 (phtalocyanine; origin: BASF AG), FLUOROL® Green Golden (perylene; origin: BASF AG).

The total amount of dyes present in the active composition may vary between 0.0% and 0.5%, preferably between 0.005% and 0.05%, the percentages being relative to the weight of the active composition.

The presence of a bittering agent may be desirable in order to render the product unpalatable, making it less likely for the active composition to be ingested, especially by young children. One can cite, as non-limiting examples, isopropyl alcohol, methyl ethyl ketone, methyl n-butyl ketone or yet a denatonium salt such as the denatonium benzoate known also under the trademark BITREX™ (origin: Mac Farlan Smith Ltd.).

The bittering agent may be incorporated in the active composition in a total amount comprised between 0.0% and 5%, the percentages being relative to the total weight of the active composition. In the case of BITREX™ the amount can be comprised between 0.0% and 0.1%, preferably between 10 and 500 ppm of the total weight of the active composition, whereas the other bittering agents above-mentioned are typically used in amounts from 0.5 to 5% by weight, when present.

In the preferred devices of the invention carrying a superstructure type emanator, the emitting part may comprise one or more emitting bodies in contact with each other, in general from one to six emitting bodies being used. Similarly, the wick part may comprise one or more wicks, in general from one to six wicks are used.

As mentioned above, the emitting part has the capacity of absorbing from 0.01 g to approximately 0.1 g of active composition per square centimeter of evaporative surface, and has a weight comprised between 80 g/m$^2$ and 1000 g/m$^2$, relative to the evaporative surface.

Preferably the emitting part has the capacity to absorb from 0.02 g to approximately 0.08 g of active volatile liquid per square centimeter of evaporative surface, and has a weight comprised between 100 g/m$^2$ and 500 g/m$^2$, relative to the evaporative surface.

The emitting part may also be characterized by an evaporative surface comprised between 50 cm$^2$ and 400 cm$^2$. Preferably, the evaporative surface will be comprised between 100 cm$^2$ and 200 cm$^2$.

Non-limiting examples of materials of which the emitting part can be made are cellulose derivatives, e.g. papers, molded ceramics, sintered or porous plastics. Textiles such as linen, cotton or yet cellulose fibers, are also convenient.

Preferred papers are those currently used as filter paper and having a particle retention size comprised between 3 μm and 30 μm, such as those commercially available from Whatman International Ltd., UK as Filter Paper N° 1, 3, 4 or 113.

In the case of sintered or porous plastics, preferably the material will have a porous size comprised between 5 μm and 200 μm and is based on high density polyethylene, ultra high molecular weight polyethylene or polypropylene. Examples of such materials are commercially available, e.g., under the tradename VYON® T (origin: Porvair Technology Ltd, UK).

The preferred diffusion materials used as the emanating surface or emanator part of the absorption/diffusion structure have the following characteristics:

| Description | Thickness (mm) | Weight (g/m$^2$) | Liquid absorbed (g/cm$^2$) |
|---|---|---|---|
| Whatman No. 1 filter paper | 0.18 | 87 | 0.005-0.010 |
| Whatman No. 3 filter paper | 0.39 | 185 | 0.012-0.024 |
| Whatman No. 4 filter paper | 0.21 | 92 | 0.008-0.016 |
| Whatman No. 113 filter paper | 0.42 | 125 | 0.015-0.030 |
| VYON ® T (sintered plastic) | 2.00 | 780 | 0.050-0.080 |

The wicking part is intended to absorb a part of the active composition and transport the latter to the emitting part, from which it can evaporate into the surrounding space of the invention's device. As mentioned previously, the wicking part may comprise between one and six wicks.

The wicking part or wick may be made of organic and inorganic materials. Examples for appropriate inorganic materials include porous porcelain materials, molded ceramics, glass fibers, or asbestos, in combination with a suitable binder such as, for example, gypsum or bentonite. It is also possible to prepare wicks from powdered mineral materials, such as, for example, clay, talc, kieselguhr, alumina, silica or the like, alone or in combination with, for example, wood flour, carbon powder, or activated carbon, using an appropriate glue. Organic materials include felt, cotton, pulp, woven and non-woven cotton fibers, synthetic fibers, cellulose derivatives, e.g. papers, and woven and non-woven sintered or porous plastics, as well as wood, possibly covered with plaster. Other details and specific examples relating to these embodiments of the invention can be found specifically in the description of International publication WO 2004/006968.

More preferred embodiments comprise wicks formed of porous natural paper material, namely pressed paper.

As mentioned previously, the device of the invention comprises powering means capable of causing movement, and more particularly rotation, of the diffusing member or assembly, thus providing forced ventilation of the diffusing surface thereof for the volatile composition. Such means may comprise a solar cell or other energy means connected to a mechanical or electrical member capable of drawing the diffusing member into movement.

The devices of the invention are preferably used in the form of air fresheners or deodorizers for rooms, cupboards preferably open to daylight in the case of solar cell powered devices, and other closed environments. They may also assume the form of animal litter refreshers, linen perfuming articles and similar. They may be presented in the form of kits of components, ready to be assembled by the user before activation of the device.

EXAMPLES

The following examples are further illustrative of the present invention embodiments, and further demonstrate the advantages of the invention devices relative to prior art teachings.

Example 1

Solar-Powered Air Freshener

With reference to FIG. 1, which illustrates an embodiment of the device of the invention, showing an exploded view of the various components of the device to be assembled, the reservoir 1, shown in cross section, is filled with a perfume solution 2 introduced through an opening in the reservoir's upper end covered by the cap 3. The opening is adapted to receive the wick part 4 of a wick/emanator assembly comprising an emitting/evaporating surface 5, in the form of shins. This emitting surface is intended for connection to the rotor member 7 via pins 6. The motor is powered by a rechargeable battery 8, which in turn is charged via a solar panel 9a lodged in the housing cap 9 of the device's housing assembly, only partially shown in the drawing (only the lower and upper caps—11, 9 respectively—being shown, in cross section view).

Before activation, the fragrance solution 2 is completely contained in the reservoir, the opening of which can be sealed via means preventing evaporation of the volatiles, as is taught for example in Applicant's international applications WO 2004/006968 and WO 2006/061803. According to the latter, specifically as described in the figures thereof, the reservoir's opening will typically be sealed by means of a lid made for example of foil and covered by a cap capable of accommodating the shape of the wick/emanator assembly (see for example FIG. 2 of WO 2004/006968).

Upon activation of the device by the user, the wick 4 penetrates the lid of the reservoir and plunges into the fragrance solution 2, thus becoming impregnated with the solution. Once the wick is saturated, the solution moves up the wick to impregnate and saturate the fins of the emanating part 5 and starts diffusing into the surroundings of the air freshener device. The cylindrical wick 4, made of a porous material capable of being impregnated with the fragrance composition 2, is lodged inside a cylindrical hollow cavity arranged in the central shaft (not represented in the drawing) of the emanator member 5, the latter being thus rotatably mounted on the wick member 4 and connected to the rotor 7.

Figure 2:
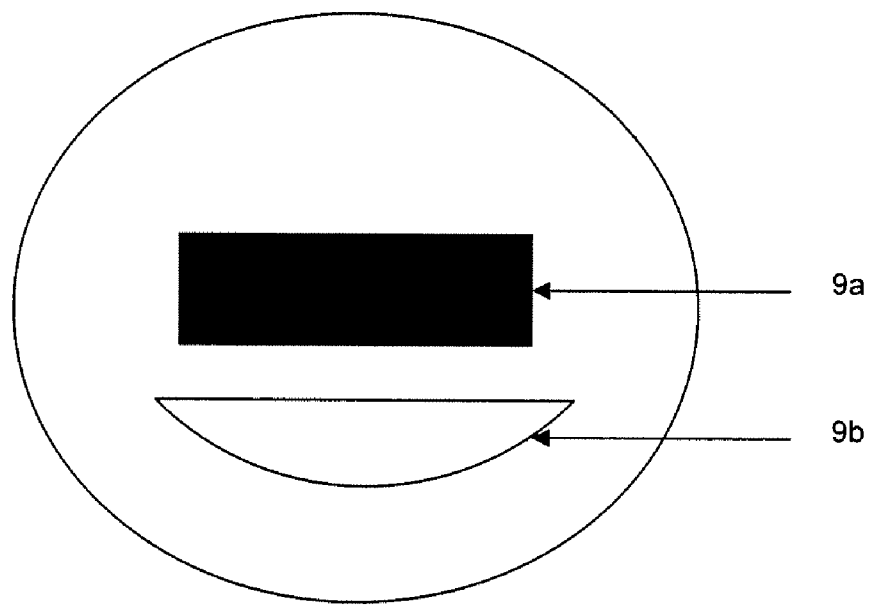
FIG. 2 is a top view of the upper cap of a housing for the device, carrying a solar panel and an on/off button for a motor intended to activate rotation of the emanating surface.

Forced evaporation of the volatile composition can be obtained by engaging the rotor 7, via an on/off button or timer 9b, located in the upper cap 9 of the device's housing assembly, next to the solar panel 9a, as represented in FIG. 2. In this manner, the user is able to select normal or accelerated evaporation of the fragrance composition, as desired.

Figure 3:
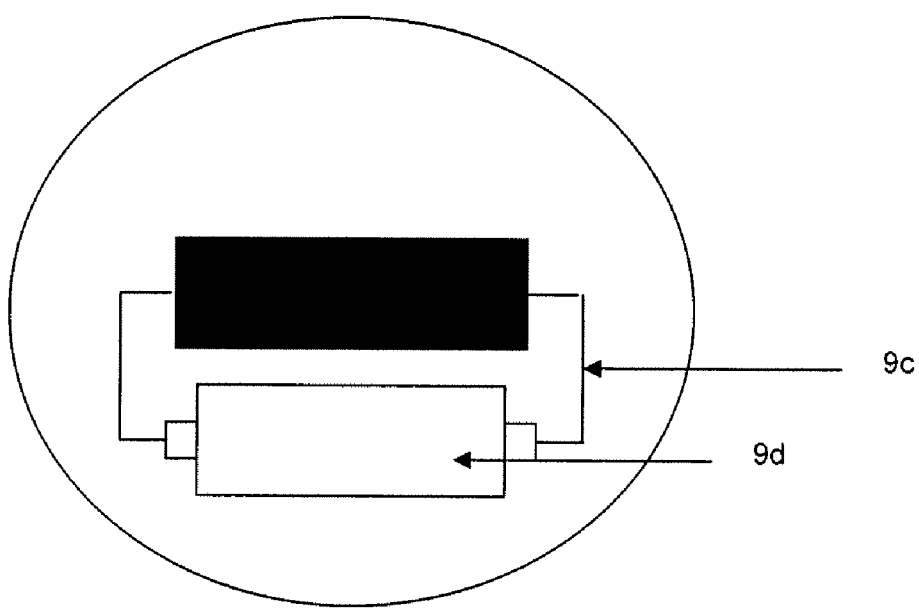
FIG. 3 is a bottom view of the internal surface of the housing's upper cap of FIG. 3, showing the connections between the solar panel and a solar-powered battery.

The solar panel 9a is connected to the battery 8 (FIG. 1), 9d (FIG. 3) via wires 9c, as represented in FIG. 3, such that the battery is charged automatically by exposure of the device to daylight, an artificial source of light, or sunlight.

Figure 4:
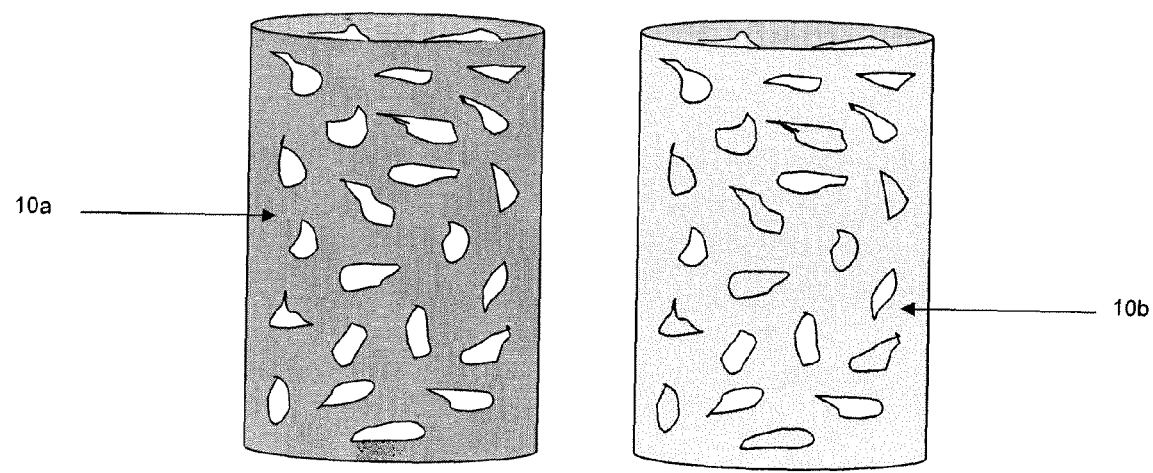
FIG. 4 is an elevated view of two vertical elements of the housing intended to be assembled together, each element being provided with vents.

The ensemble formed by the reservoir, the wick/emanator assembly, the rotor member and the rechargeable battery is lodged inside the device's housing. The latter can be formed of two hollow, cylindrical vertical parts, both provided with carved vents or openings, as represented in FIG. 4. The inner part 10b of the housing ensemble is assembled over the wick/emanator assembly and is secured in place between the bottom and top caps 9 and 11 of the housing. The outer part 10a of the housing member, forming a movable shutter equipped with vents, is snapped into place between these two caps, in a manner allowing it to be moved relative to the inner housing part 10b, so as to control the exposure of the fin shaped surface of the rotatable emanator 5 to the surrounding atmosphere. The amount of evaporation can be controlled via the further or lesser coincidence of these vents, together with the actioning, or not, of the rotor which engages into rotation the emanator 5 and thus forces increased evaporation of the perfume composition deposited on the evaporation surface.

It goes without saying that a similar form of the device can be realized without the solar panel, the motor being powered by a replaceable battery for example.

Figure 5:
FIG. 5 is a perspective view of the invention's closed air-freshener, in a form ready for commercialization.
Figure 6:
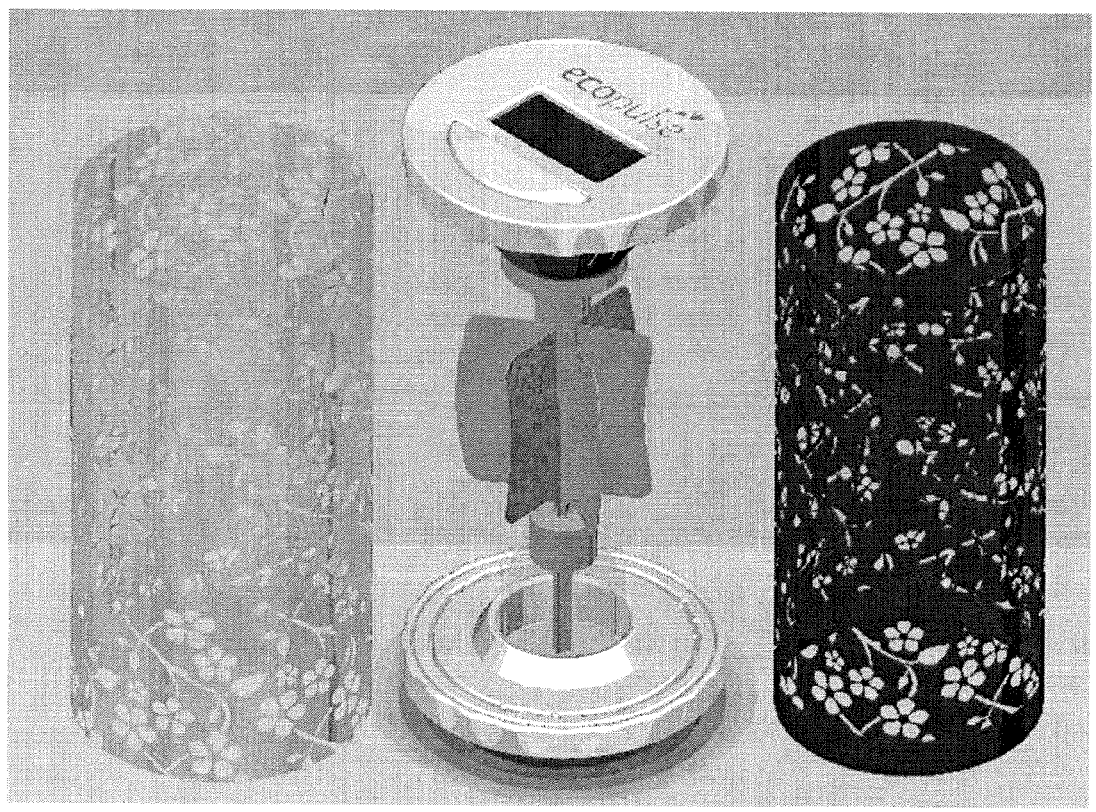
FIG. 6 shows a perspective view of the assembled inner contents of the device, to be covered with the inner and outer components of the device's housing assembly, provided with vents.

The closed air-freshener, in a form susceptible of commercialization, is shown on FIG. 5, whereas FIG. 6 shows a perspective view of the assembled inner contents of the device, to be covered with the inner and outer vented components of the device's housing assembly, represented on both sides of the wick/emanator, plus reservoir assembly.

Example 2

Figure 7:
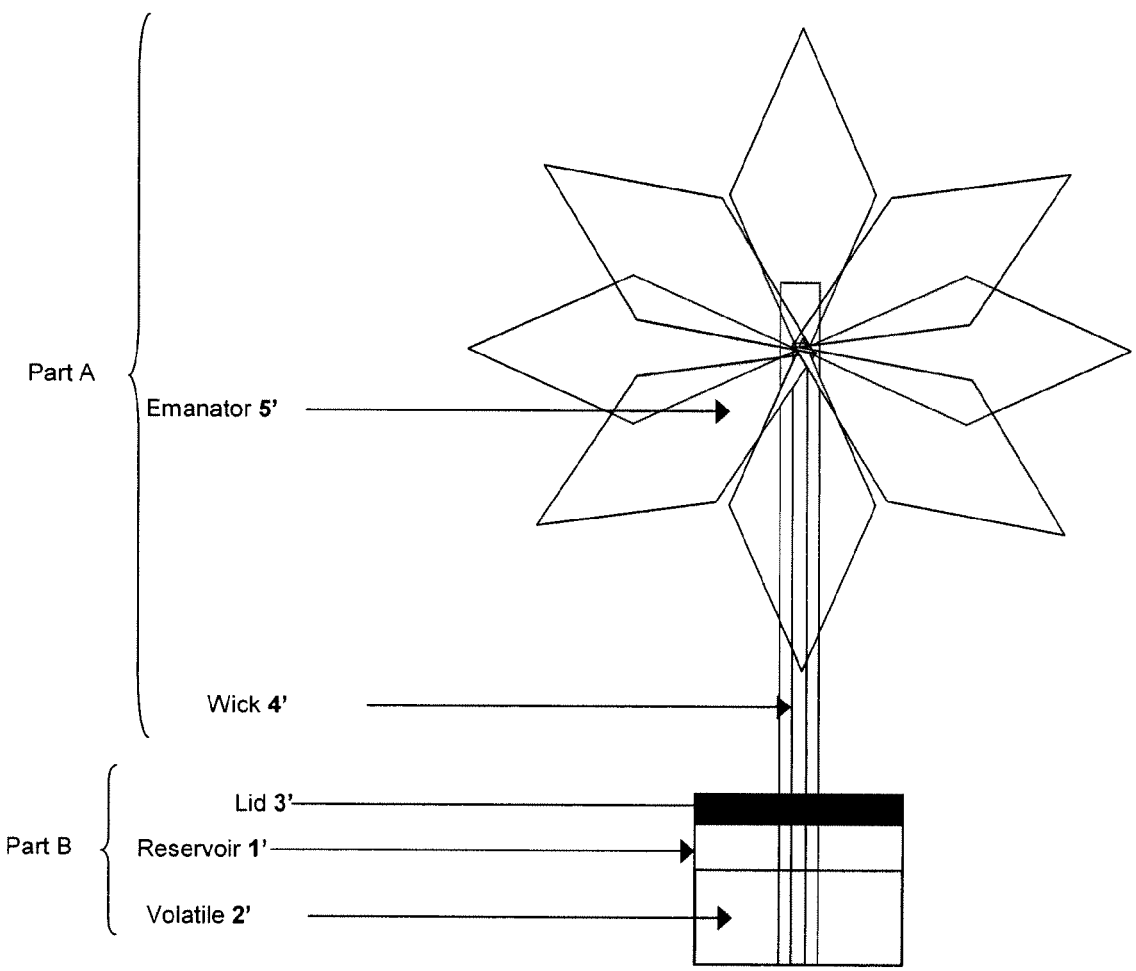
FIG. 7 is a cross-section view of another embodiment of an assembled device according to the invention, without the housing member.

With reference to FIG. 7, which illustrates another embodiment of the device of the invention, showing an alternative design of the rotatable emanator member of the wick/emanator assembly, the reservoir 1' contains the active liquid volatile composition 2', into which is plunged the wick 4'. The latter is lodged inside a hollow cavity of the central shaft on which a star-shaped emanator/evaporation member 5' is rotatably mounted in a manner allowing for further connection of the emanator to a rotor not represented in the figure. The inner parts of the device are thus shown in an already assembled form.

Example 3

Figure 8:
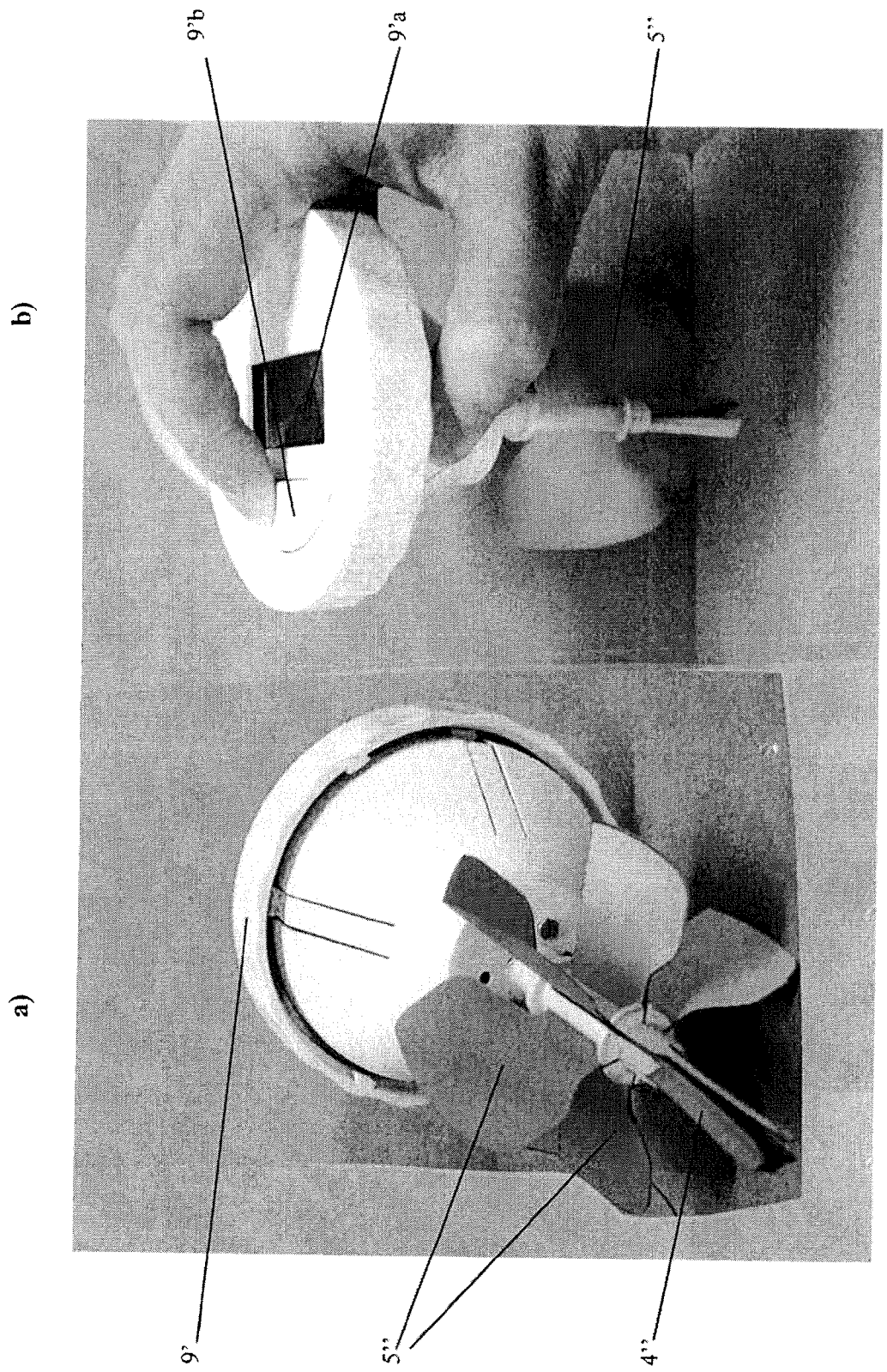
FIGS. 8 a) and b) show a perspective view of yet another embodiment of the wick/emanator assembly already mounted on the upper part of the device, in a static, respectively moving status.

With reference to FIG. 8, which shows an embodiment of an assembled moveable wick/emanator part of the device, there is illustrated in FIG. 8 a) this embodiment when in a static status.

The wick member 4", made of several components, is arranged coaxially with the central shaft of the device, the latter being connected to the powered motor (not shown in the figure), and in contact with a shin-formed emanatory member 5", rotatably mounted on the shaft. As shown in FIG. 8 b), upon the user's pressure on the on/off button 9'b located on the cap 9', the emanator member enters into rotation, activated by the rotor powered via the solar panel 9'a.

What is claimed is:

1. A device for dispensing an active volatile substance into the surrounding atmosphere, provided with means for forced ventilation of an evaporation surface impregnated with the volatile substance, the device comprising:

a reservoir containing the active volatile substance and having an upper part equipped with an opening;

a wick/emanating member assembly comprising an emanating member carrying the evaporation surface and formed of a material capable of being impregnated with the active volatile substance upon activation of the device and of allowing evaporation thereof into air surrounding the device; and a wick member formed of, or carrying, a porous material part capable of being impregnated with the active volatile substance, the wick member being adapted to be lodged in the device through the opening of the reservoir's upper part in a position allowing it to be impregnated with the volatile substance and to be in contact with the emanating member, wherein, upon activation of the device, the emanating member and the wick member are lodged in the device in a position allowing the wick member to be in contact with the active volatile substance and to cause the emanating member to be impregnated therewith, and wherein the means for forced ventilation of the evaporation surface carried by the emanating member is operatively associated with the wick/emanating member assembly and comprises electrically, battery or solar powered means for providing repeated, rotating movement of at least the emanating member for a determined period of time, relative to the reservoir, with the device being devoid of any moving parts capable of causing forced ventilation other than the emanating member or wick/emanating member assembly.

2. The device of claim 1, further comprising a housing assembly covering at least the emanating member, the housing assembly comprising means to allow diffusion of the active volatile into air surrounding the device upon its activation.

3. The device of claim 2, further comprising an on/off button or timer accessible to a user from the outside of the device and intended for activating the powered means for causing motion of at least the emanating member.

4. The device of claim 2, wherein the housing assembly comprises two vertical elements, an internal part and an external part, both being provided with openings or vents, the two parts being moveably arranged so as to be able to slide relative to each other upon activation of the device, to allow partial or total overlap of the inner and outer vents.

5. The device of claim 1, wherein the active volatile substance is a liquid comprising a perfume, a deodorizing substance, an insecticide substance, an insect repellent or attracting substance, an antibacterial or bacteriostatic agent.

6. The device of claim 5, wherein the active volatile liquid is a non-aqueous liquid perfuming composition, at least 60% of the total weight of which is formed of ingredients having a vapor pressure comprised between 4 PA and 270 PA at 20° C.

7. The device of claim 1, wherein the emanating member has a weight of between 80 and 1000 grams per square meter of evaporative surface, and an absorbency of between 0.01 and 0.1 grams of active volatile liquid composition per square centimeter of evaporative surface.

8. The device of claim 7, wherein the emanating or evaporative surface of the emanating member is between 50 $cm^2$ and 400 $cm^2$.

9. The device of claim 5, wherein the active volatile liquid further comprises one or more ingredients selected from the group consisting of solvents, thickeners, anti-oxidants, dyes, bittering agents and UV inhibitors.

10. A consumer article, comprising the device of claim 1 together with an appropriate packaging.

11. The consumer article of claim 10, in the form of an air freshener, a mothproofer, an insecticide or an insect repellent device, or a combination thereof.

12. The consumer article of claim 10 wherein separate packaging is provided for the volatile substance reservoir and the wick/emanating member assembly or the packaging includes separate compartments of a single packaging for separating the volatile substance reservoir and the wick/emanating member assembly.

13. A device for dispensing an active volatile substance into the surrounding atmosphere, provided with a forced ventilation mechanism for ventilating an evaporation surface impregnated with the volatile substance, the device comprising:

a reservoir containing the active volatile substance and having an upper, part equipped with an opening;

a wick/emanating member assembly comprising an emanating member carrying the evaporation surface and formed of a material capable of being impregnated with the active volatile substance upon activation of the device and of allowing evaporation thereof into air surrounding the device; and a wick member formed of, or carrying, a porous material part capable of being impregnated with the active volatile substance, the wick member being adapted to be lodged in the device through the opening of the reservoir's upper part in a position allowing it to be impregnated with the volatile substance and to be in contact with the emanating member, wherein, upon activation of the device, the emanating member and the wick member are lodged in the device in a position allowing the wick member to be in contact with the active volatile substance and to cause the emanating member to be impregnated therewith, and wherein the forced ventilation mechanism is operatively associated with the wick/emanating member assembly and is powered electrically, by battery or by solar power and includes a rotor that provides continuous rotation of one of the wick/emanating member assembly or the emanating member for a determined period of time, relative to the reservoir, with the rotation of the emanating member or of the wick/emanating member assembly being the sole moving part of the device for causing the forced ventilation.

14. The device of claim 13, which further comprises a housing assembly within which is lodged the wick/emanating member assembly, the housing assembly carrying a solar panel lodged in a housing cap thereof and means allowing connection of the solar panel to a battery intended for powering the rotor connected to at least the emanating member and able to cause rotation thereof.

15. The device of claim 13, wherein the wick/emanating member assembly is formed of a single piece, both the wick member and the emanating member being susceptible of being engaged into rotation.

16. The device of claim 13, wherein the reservoir carries a cap or lid assembly provided with a supporting shaft on which the emanating member is arranged, the shaft having a hollow cavity for lodging the wick member.

17. The device of claim 16, wherein the emanating member is fin-shaped or star-shaped.

18. The device of claim 17, wherein the emanating member is star shaped and rotatably mounted on the shaft.

19. The device of claim 16, wherein the wick member and the emanating member are coaxially arranged on the shaft, which also supports the rotor member.

\* \* \* \* \*